United States Patent [19]
Barrett et al.

[11] Patent Number: 6,166,083
[45] Date of Patent: Dec. 26, 2000

[54] SUCKABLE FLURBIPROFEN LOZENGES FOR TREATMENT OF SORE THROAT

[75] Inventors: David Michael Barrett; Carl Simon Smith; David Michael Thurgood, all of Nottingham, United Kingdom

[73] Assignee: The Boots Company, PLC, Nottingham, Canada

[21] Appl. No.: 09/224,357

[22] Filed: Jan. 4, 1999

Related U.S. Application Data

[62] Division of application No. 08/849,224, filed as application No. PCT/EP96/05208, Nov. 21, 1996, Pat. No. 5,889,057.

[30] Foreign Application Priority Data

Nov. 22, 1995 [GB] United Kingdom ............ 9523833

[51] Int. Cl.$^7$ .................................................. A61K 31/19
[52] U.S. Cl. .................................................... 514/570
[58] Field of Search ......................................... 514/570

[56] References Cited

U.S. PATENT DOCUMENTS

| | | |
|---|---|---|
| 4,389,393 | 6/1983 | Schor . |
| 4,931,473 | 6/1990 | Kelleher et al. ............ 514/688 |
| 5,190,981 | 3/1993 | Wrechter . |
| 5,206,029 | 4/1993 | Brune . |
| 5,458,879 | 10/1995 | Singh . |
| 5,567,733 | 10/1996 | Dishler ........................ 514/567 |

FOREIGN PATENT DOCUMENTS

| | | |
|---|---|---|
| 0137668 | 4/1985 | European Pat. Off. . |
| 0228223 | 7/1987 | European Pat. Off. . |
| 0 426618 | 1/1992 | Japan . |
| 1527563 | 10/1978 | United Kingdom . |
| WO 88/03021 | 5/1988 | WIPO . |
| WO 91/02512 | 3/1991 | WIPO . |
| WO 92/00725 | 1/1992 | WIPO . |
| WO 94/13280 | 6/1994 | WIPO . |
| WO 95/23591 | 9/1995 | WIPO . |
| WO 96/07412 | 3/1996 | WIPO . |
| WO 97/2273 | 1/1997 | WIPO . |
| WO 97/18802 | 5/1997 | WIPO . |
| WO 94/14476 | 7/1997 | WIPO . |
| WO 97/38662 | 10/1997 | WIPO . |
| WO 97/38663 | 10/1997 | WIPO . |

OTHER PUBLICATIONS

Patent Abstracts of Japan, vol. 018, No. 061 (C–1160), JP 05 279250A (Osaka Aerosol Ind. Corp.) Oct. 26, 1993.

Hahn R.: "Clinical evaluation of flurbiprofen alone and plus ampicillin in chronic pharyngitis in acute phase" Int. J. Clin. Pharmacol. Res., vol. 6, No. 1, 1986, pp. 81–86, XP002078978.

Chemical Abstracts, vol. 112, No. 24, Jun. 11, 1990 Columbus, Ohio US; abstract No. 223137, Motono M.: "Manuafcture of topical cosmetics and pharmaceutical containing ginger extracts as absortion accelerators" XP002078980.

Patent Abstracts fo Japan, vol. 13, No. 501 & JP 01 199916 A (Sansho Seiyaku Co. Ltd), Aug. 11, 1989.

Mira et al.: "Treatment of pharyngitis and pharyngolaryngitis. comparison of phenylprenazone and flurbiprofen administered orally and rectally" Clin. Trials J., vol. 21, No. 2, 1984, pp. 100–108, XP002078797.

Derwent Publication XP–002078972, 1990.
Derwent Publication XP–002078973, 1986.
Derwent Abstract 91–328376, 1989.
Derwent Abstract 88–223002, 1986.

Cadeddu et al., Biological Abstracts, vol. 87, abstracts No. 63515, 1988.

*Development of an Ibuprofen Lozenge for the Elderly*, By M.L. Wilson, W.A. Ritschel, and A. Sakr; Pharm. Ind. 56, Nr.9 (1994) Wilson et al.—Ibuprofen; pp. 836–841.

*Development of an Ibuprofen Lozenge for the Elderly*, By M.L. Wilson, W.A. Ritschel, and A. Sakr; Drugs made in Germany 38, No. 3 (1995) Wilson et al—Ibuprofen lozenge; pp. 90–95.

Wilson et al, Derwent Drug File Abstracts, abstract No. 1992–13831, 1991.

*Primary Examiner*—William R. A. Jarvis
*Attorney, Agent, or Firm*—Arent Fox Kintner Plotkin Kahn, PLC

[57] ABSTRACT

This invention relates to a sugar based or sugar alcohol-based suckable lozenge of the non-steroidal antiinflammatory drug flurbiprofen for the treatment of soar throat.

2 Claims, No Drawings

SUCKABLE FLURBIPROFEN LOZENGES FOR TREATMENT OF SORE THROAT

This application is a divisional application of U.S. Ser. No. 08/849,224, filed Jun. 16, 1997, now U.S. Pat. No. 5,889,057, which is a 371 of PCT/EP96/05208, filed Nov. 21, 1996.

The present invention relates to a new medical use of flurbiprofen. Flurbiprofen [2-(2-fluoro4-biphenylyl) propionic] acid is a well known non-steroidal anti-inflammatory drug which also has analgesic and antipyretic activity. The flurbiprofen molecule exists in two enantiomeric forms and the term flurbiprofen as used herein is intended to embrace the individual enantiomers and mixtures thereof in any proportion including a 1:1 mixture which is herein referred to as racemic flurbiprofen. Flurbiprofen can exist in the form of pharmaceutically acceptable salts or in the form of derivatives such as esters and such salts or esters are embraced by the term "flurbiprofen" as used herein.

Flurbiprofen and its S(+) enantiomer have been proposed for treating medical conditions of the gums.

EP 137668-A (Upjohn) describes the use of flurbiprofen for preventing or inhibiting alveolar bone resorption.

EP 486561-A (Sepracor) describes the use of S(+)-flurbiprofen to treat periodontal disease and to promote bone regrowth associated with the disease. Periodontal disease is stated to include periodontitis, gingivitis and periodontosis.

Both these documents specifically describe the treatment of the gums and do not relate to any other part of the oral cavity.

The present invention relates to the use of flurbiprofen in the treatment of sore throats which comprises the administration to a patient in need of such treatment of a pharmaceutical composition in the form of a masticable or suckable solid dosage form or a spray containing a therapeutically effective amount of flurbiprofen which releases the flurbiprofen in the oral cavity so as to deliver the flurbiprofen to the surface of the sore throat.

The solid dosage form may be a lozenge which is intended to be sucked by the patient or a masticable or suckable table capsule, pastille or gum, for example chewing gum. The term "lozenge" as used herein is intended to embrace all dosage forms where the product is formed by cooling a sugar-based or sugar alcohol based (eg sorbitol) molten mass containing the active material. The term "tablet" as used herein is intended to embrace unit dosage forms made from compressed powders or granules or compressed pastes. A preferred pharmaceutical composition is a lozenge prepared by cooling a heated lozenge base comprising sugar, liquid glucose, flurbiprofen and other excipients to form solid lozenges.

The therapeutically effective amount has been found to be from 5% to 40% of the normal adult dose when given by ingestion to achieve a systemic antiinflammatory and/or analgesic effect. Flurbiprofen may therefore be present in the pharmaceutical composition in an amount from 2.5 to 20 mg preferably 5 to 12.5 mg, Where a pharmaceutically acceptable salt of flurbiprofen is used, the amount of the salt used should be such as to provide the desired amount of flurbiprofen. Suitable salts include the alkali metal salts eg the sodium salt or amino acid salts eg the lysine, arginine or meglumine salts of flurbiprofen.

Flurbiprofen would be expected, in common with other non-steroidal anti-inflammatory agents to cause an unpleasant burning sensation at the back of the mouth when retained in the mouth. This would clearly be unacceptable to the patient being treated. The present applicants have surprisingly found that an unacceptable burning sensation is not experienced when the present invention is used to treat a sore throat but that the patient does receive relief of the symptoms of the sore throat.

Solid dosage forms may be prepared by methods which are well known in the art for the production of lozenges, tablets, capsules or chewing gums and may contain other ingredients known in such dosage forms such as acidity regulators, opacifiers, stabilising agents, buffering agents, flavourings, sweeteners, colouring agents, buffering agents, flavourings, sweeteners, colouring agents and preservatives. For example, the preferred solid formulations of the present invention may be prepared as lozenges by heating the lozenge base (eg a mixture of sugar and liquid glucose) under vacuum to remove excess water and the remaining components are then blended into the mixture. The resulting mixture is then drawn into a continuous cylindrical mass from which the individual lozenges are formed. The lozenges are then cooled, subjected to a visual check and packed into suitable packaging. One form of suitable packaging is a blister pack of a water-impermeable plastics material (eg polyvinylchloride) closed by a metallic eg aluminium foil. The patient removes the lozenge by applying pressure to the blister to force the lozenge to rupture and pass through the metal foil seal. Lozenges will normally be sucked by the patient to release the flurbiprofen. Masticable solid dose formulations may be made by the methods used to prepare chewable candy products or chewing gums. For example, a chewable solid dosage form may be prepared from an extruded mixture of sugar and glucose syrup to which the flurbiprofen has been added with optional addition of whipping agents, humectants, lubricants, flavours and colourings. (See Pharmaceutical Dosage Forms: Tablets, Volume 1, Second Edition edited by H A Lieberman, L Lachman and J B Schwartz published in 1989).

Spray formulations may be prepared by dissolving or suspending the flurbiprofen in a liquid medium which may also contain other ingredients such as stabilising agents, buffering agents, flavourings, sweeteners, colouring agents, buffering agents, flavourings, sweeteners, colouring agents and preservatives. For example, a spray may be prepared by dissolving water soluble components in water and non-water soluble ingredients in a co-solvent (eg alcohol). The two phases are then mixed and the resulting mixture filtered and placed into dispensing containers. The dispensing containers may be fitted with a metered, manually-operated spray mechanism or the dispenser may contain a pressurised propellant and be fitted with a suitable dispensing valve.

One form of preferred formulations for use in the present invention are compositions which can be sucked or chewed by the patient and which slowly release the flurbiprofen. The flurbiprofen then passes over the mucous membrane of the throat where some is absorbed providing topical relief. The unabsorbed flurbiprofen is then ingested by the patient and absorbed into the blood stream. The flurbiprofen so absorbed can act systematically to provide analgesia, anti-inflammatory and anti-pyretic activity in addition to the relief that comes from the topical application of flurbiprofen to the mucous membrane of the throat.

A second form of preferred formulations for use in the present invention are sprays which are administered so that the liquid composition is brought into contact with the mucus membrane of the throat so that some of the active ingredient is absorbed providing topical relief. Ingestion of the liquid composition then means that the unabsorbed flurbiprofen can be absorbed in to the blood stream to provide systemic analgesic, anti-inflammatory or antipyretic activity in addition to the relief that comes from the topical application of flurbiprofen to the mucous membrane of the throat.

The invention will be illustrated by the following Examples which are given by way of example only.

EXAMPLES 1 to 4

Lozenges were prepared containing the following ingredients expressed as the weight in milligrammes per lozenge.

|  | Ex 1 | E 2 | Ex 3 | Ex 4 |
|---|---|---|---|---|
| Racemic flurbiprofen | 2.5 | 5 | 8.75 | 12.5 |
| Flavouring (cherry) | 7.05 | 7.05 | 7.05 | 7.05 |
| Calcium carbonate | 7.5 | 7.5 | 7.5 | 7.5 |
| Silicon Dioxide (Aerosil 300) | 0.75 | 0.938 | 0.94 | 1.5 |
| Solids from a 1:1 mixture of sugar and liquid glucose | to 2350 | to 2350 | to 2350 | to 2350 |

The mixture of the sugar and liquid glucose was heated to 140° and a vacuum applied to reduce the water content of the mixture. The flavouring was added in a sealed vessel. The flurbiprofen, silicon dioxide (flow aid) and calcium carbonate were blended and the blend added to the remainder of the ingredients. The resulting mixture was cooled and formed into a continuous cylindrical mass from which the individual lozenges were formed. The individual solid lozenges were visually inspected and then packed.

The resulting lozenges were found to provide palatable, stable and effective treatment for sore throats.

EXAMPLES 5 to 7

In a similar manner to that described in Examples 1 to 4 above, lozenges were made containing the following ingredients expressed as the weight in milligrammes per lozenge.

|  | Ex 5 | Ex 6 | Ex 7 |
|---|---|---|---|
| Racemic flurbiprofen | 5 | 8.75 | 12.5 |
| Levomenthol | 4 | 4 | 4 |
| Flavouring (orange) | 1.645 | 1.645 | 1.645 |
| Flavouring (grapefruit) | 2.5 | 2.5 | 2.5 |
| Sodium saccharin | 2 | 2 | 2 |
| Calcium Carbonate | 7.5 | 7.5 | 7.5 |
| Silicon Dioxide (Aerosil 300) | 0.94 | 1.22 | 1.5 |
| Solids from a 1:1 mixture of sugar and liquid glucose | to 2350 | to 2350 | to 2350 |

EXAMPLES 8 and 9

In a similar manner to that described in Examples 1 to 4 above, lozenges were made containing the following ingredients expressed as the weight in milligrammes per lozenge.

|  | Ex 8 | Ex 9 |
|---|---|---|
| Racemic Flurbiprofen | 5 | 12.5 |
| Levomenthol | 1.551 | 1.551 |
| Flavouring (orange) | 1.645 | 1.645 |
| Peppermint Oil | 2 | 2 |
| Aspartame | 4 | 4 |
| Calcium Carbonate | 7.5 | 7.5 |
| Silicon Dioxide (Aerosil 300) | 0.94 | 1.5 |
| Solids from a 1:1 mixture of sugar and liquid glucose | to 2350 | to 2350 |

EXAMPLES 10 and 11

In a similar manner to that described in Examples 1 to 4 above, lozenges were made containing the following ingredients expressed as the weight in milligrammes per lozenge.

|  | Ex 10 | Ex 11 |
|---|---|---|
| Racemic Flurbiprofen | 5 | 12.5 |
| Levomenthol | 4 | 4 |
| Flavouring (orange) | 1.645 | 1.645 |
| Flavouring (lime) | 2.5 | 2.5 |
| Aspartame | 4 | 4 |
| Calcium Carbonate | 7.5 | 7.5 |
| Silicone Dioxide (Aerosil 300) | 0.94 | 1.5 |
| Solids from a 1:1 mixture of sugar and liquid glucose | to 2350 | to 2350 |

EXAMPLES 12 and 13

In a similar manner to that described in Examples 1 to 4 above, lozenges were made containing the following ingredients expressed as the weight in milligrammes per lozenge.

|  | Ex 12 | Ex 13 |
|---|---|---|
| Racemic Flurbiprofen | 5 | 12.5 |
| Levomenthol | 4 | 4 |
| Flavouring (lime) | 2.5 | 2.5 |
| Aspartame | 4 | 4 |
| Calcium Carbonate | 7.5 | 7.5 |
| Silicon Dioxide (Aerosil 300) | 0.94 | 1.5 |
| A 1:1 mixture of sugar and liquid glucose | to 2350 | to 2350 |

EXAMPLE 14

The following components were mixed to provide a pharmaceutical formulation which can be packed into a dispensing container fitted with a metered manually-operated spray mechanism which enables the formulation to be sprayed on to the mucus membrane of the throat as a fine spray. All percentages are by weight of the final formulation.

| Racemic Flurbiprofen | 0.624% |
|---|---|
| Alcohol | 34.71% |
| Sorbitol (70% solution) | 13.90% |
| Glycerin | 13.58% |
| Colours, flavouring | qs |
| Water | to 100% |

The effectiveness of the treatment has been demonstrated by means of clinical trials in which patients suffering from sore throats are administered the formulations described in one of Examples 2, 3 and 4 or a placebo. The patient was asked to assess the effectiveness of the treatment on parameters such as the relief of the pain associated with the sore throat, the reduction in the swelling of the throat and/or the improvement in swallowing following treatment. The patients were also examined by a clinician to determine the amount of tonsillopharyngitis.

What is claimed is:

1. A suckable solid dosage form, comprising 2.5 to 20 mg of flurbiprofen contained in a lozenge base formed by cooling a sugar-based or sugar alcohol-based molten mass, such that when the dosage form is administered to the oral cavity of a patient in need thereof and sucked, the solid dosage form releases a therapeutically effective amount of flurbiprofen to the oral cavity so as to deliver said flurbiprofen to the surface of the throat of said patient for the treatment of sore throat.

2. A solid dosage form as claimed in claim 1, comprising 5 to 12.5 mg of flurbiprofen.

* * * * *

UNITED STATES PATENT AND TRADEMARK OFFICE
CERTIFICATE OF CORRECTION

PATENT NO. : 6,166,083

DATED : December 26, 2000

INVENTOR(S) : David Michael BARRETT et al.

It is certified that error appears in the above-identified patent and that said Letters Patent is hereby corrected as shown below:

ON THE TITLE PAGE

[73] Change ``Canada'' to --United Kingdom--.

Signed and Sealed this

Twenty-ninth Day of May, 2001

Attest:

NICHOLAS P. GODICI

Attesting Officer

Acting Director of the United States Patent and Trademark Office